United States Patent [19]

VandenBerg

[11] Patent Number: Plant 7,465

[45] Date of Patent: Mar. 5, 1991

[54] CHRYSANTHEMUM PLANT NAMED MELOSA

[75] Inventor: Cornelis P. VandenBerg, Salinas, Calif.

[73] Assignee: Yoder Brothers, Inc., Barberton, Ohio

[21] Appl. No.: 408,326

[22] Filed: Sep. 18, 1989

[51] Int. Cl.[5] ..... A01H 5/00

[52] U.S. Cl. ..... Plt./80

[58] Field of Search ..... Plt./80, 81

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Melosa particularly characterized by its flat capitulum form; decorative capitulum type; soft lavender-pink ray floret color; diameter across face of capitulum of up to 9.5 cm at maturity; uniform eight week photoperiodic flowering response to short days; peduncle length ranging from 10 to 20 cm on open, terminal sprays; medium plant height when grown as a single stem spray cut mum; and excellent tolerance to low temperatures for bud initiation and flower development.

3 Drawing Sheets

1

The present invention comprises a new and distinct cultivar of Chrysanthemum, botanically known as *Dendranthema grandiflora,* and referred to by the cultivar name Melosa.

Melosa, identified a 85-268008, was originated from a cross made by Cornelis P. VandenBerg in a controlled breeding program in Salinas, Calif., in 1984.

The female parent of Melosa was an unnamed cut spray mum seedling identified as 81-671002, having yellow ray floret color, decorative capitulum type, ten (10) week photoperiodic flowering response to short days, and medium height. The male parent of Melosa was also an unnamed cut spray mum seedling, identified as 82-J38047, having white ray floret color, decorative duplex capitulum type, eight week photoperiodic flowering response to short days, and medium plant height.

Melosa was discovered and selected as one flowering plant within the progeny of the stated cross by Cornelis P. VandenBerg in March, 1986, in a controlled environment in Salinas, Calif.

The first act of asexual reproduction of Melosa was accomplished when vegetative cuttings were taken from the initial selection in May, 1986 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Melosa are firmly fixed and are retained through successive generations of asexual reproduction.

Melosa has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Colombia.

The following traits have been repeatedly observed and are determined to be basic characteristics of Melosa, which, in combination, distinguish this Chrysanthemum as a new and distinct cultivar:

2

1. Flat capitulum form.
2. Decorative capitulum type.
3. Soft lavender-pink ray floret color.
4. Diameter across face of capitulum up to 9.5 cm at maturity.
5. Unifom eight week photoperiodic flowering response to short days.
6. Peduncle length ranging from 10 to 20 cm on open terminal sprays.
7. Medium plant height, requiring two long day weeks prior to short days to attain a flowered plant height of 90 to 100 cm for year-round flowerings.
8. Excellent tolerance to low temperatures for bud initiation and flower development.

The accompanying photograhic drawings show typical inflorescence and leaf characteristics of Melosa, with the colors being as nearly true as possible with illustrations of this type. Sheet 1 is a color photograph of Melosa grown as a single stem cut spray mum. Sheet 2 is a black and white photograph of three views of the inflorescence of Melosa. Sheet 3 is a black and white photograph showing the upper and under sides of the leaves of Melosa at three stages of development (mature, intermediate and immature).

Of the commercial cultivars known to the inventor, the most similar in comparison to Melosa is the cultivar identified as Beloved, disclosed in U.S. Plant Pat. No. 3,741. Reference is made to attached Chart A, which compares certain characteristics of Melosa to the same characteristics of Beloved.

Similar traits are capitulum form and type, peduncle length and plant height. Melosa has a lighter flower color, a more upright spray formation, a larger diameter of capitulum, a faster flowering response and better low temperature tolerance than Beloved.

In the following description color references are made to the Royal Horticultural Society Color Chart. The color values were determined on plant material grown in Salinas, Calif. on Apr. 26, 1989.

Classification:

*Botanical.*—*Dendranthema grandiflora* cv Melosa.

*Commercial.*—Decorative cut spray mum.

INFLORESCENCE

A. Capitulum:

*Form.*—Flat.

*Type.*—Decorative.

*Diameter across face.*—Up to 9.5 cm at maturity.

B. Corolla of ray florets:

*Color (general tonality from a distance of three meters).*—Soft lavender-pink.

*Color (upper surface).*—56A to 56C.

*Color (under surface).*—56C.

*Shape.*—Longitudinal slightly reflexing. Cross-section slightly concave.

C. Corolla of disc florets:

*Color (mature).*—Closest to 14A.

*Color (immature).*—Closest to 145C.

D. Reproductive organs:

*Androecium.*—Present on disc florets only; very few disc florets, barely visible in the mature flower; scant pollen.

*Gynoecium.*—Present on both ray and disc florets.

PLANT

A. General Appearance:

*Height.*—Medium; 90 to 100 cm as a single stem cut mum with two long day weeks prior to short days.

B. Foliage:

*Color (upper surface).*—147A.

*Color (under surface).*—147B.

*Shape.*—Deeply lobed, slightly serrated.

CHART A

COMPARISON OF MELOSA AND BELOVED

| | MELOSA | BELOVED |
|---|---|---|
| Ray Floret Color | Soft lavender-pink | Lavender |
| Capitulum Form and Type | Flat decorative | Flat decorative |
| Spray formation | Terminal, upright | Terminal, wide |
| Peduncle length | 10 to 20 cm | 10 to 20 cm |
| Diameter Across Face of Capitulum | Up to 9.5 cm | Up to 8.3 cm |
| Plant Height | Medium | Medium |
| Flowering response period | 8 weeks | 9 weeks |
| Low temperature tolerance | Good | Marginal |

Comparisons Made of Plants Grown As Single Stem Spray Cut Mums In Salinas, California

I claim:

1. A new and distinct Chrysanthemum plant named Melosa, as described and illustrated.

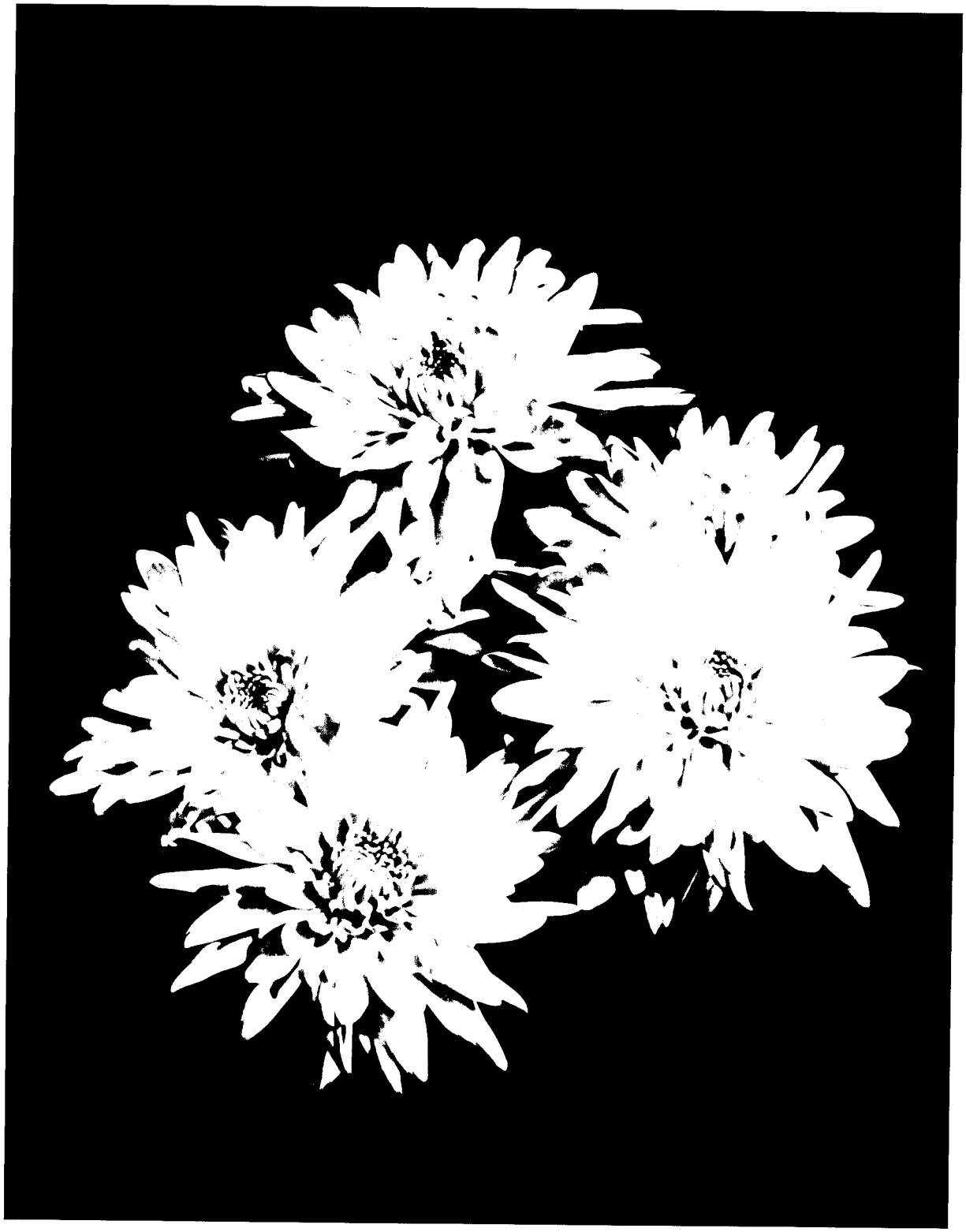

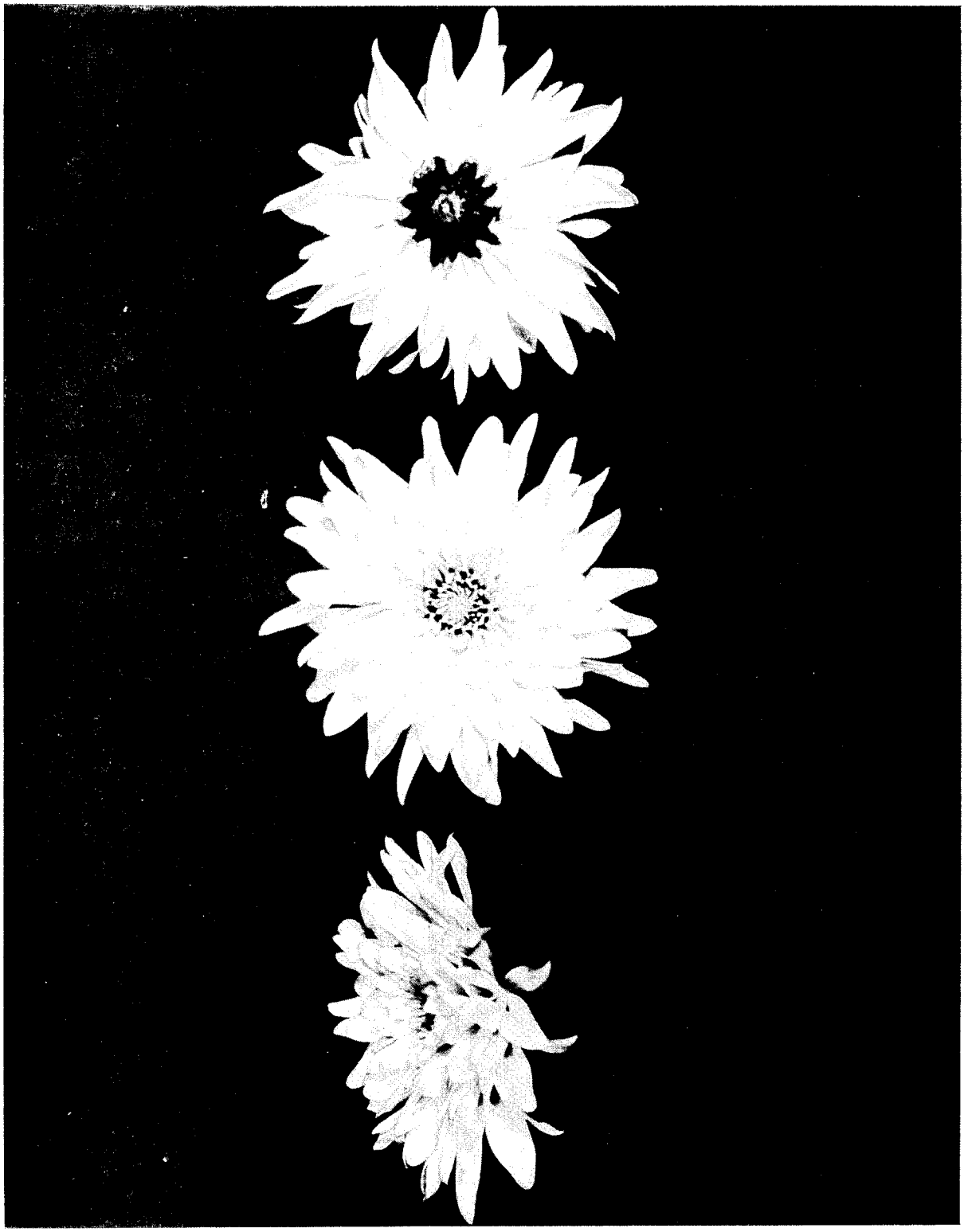

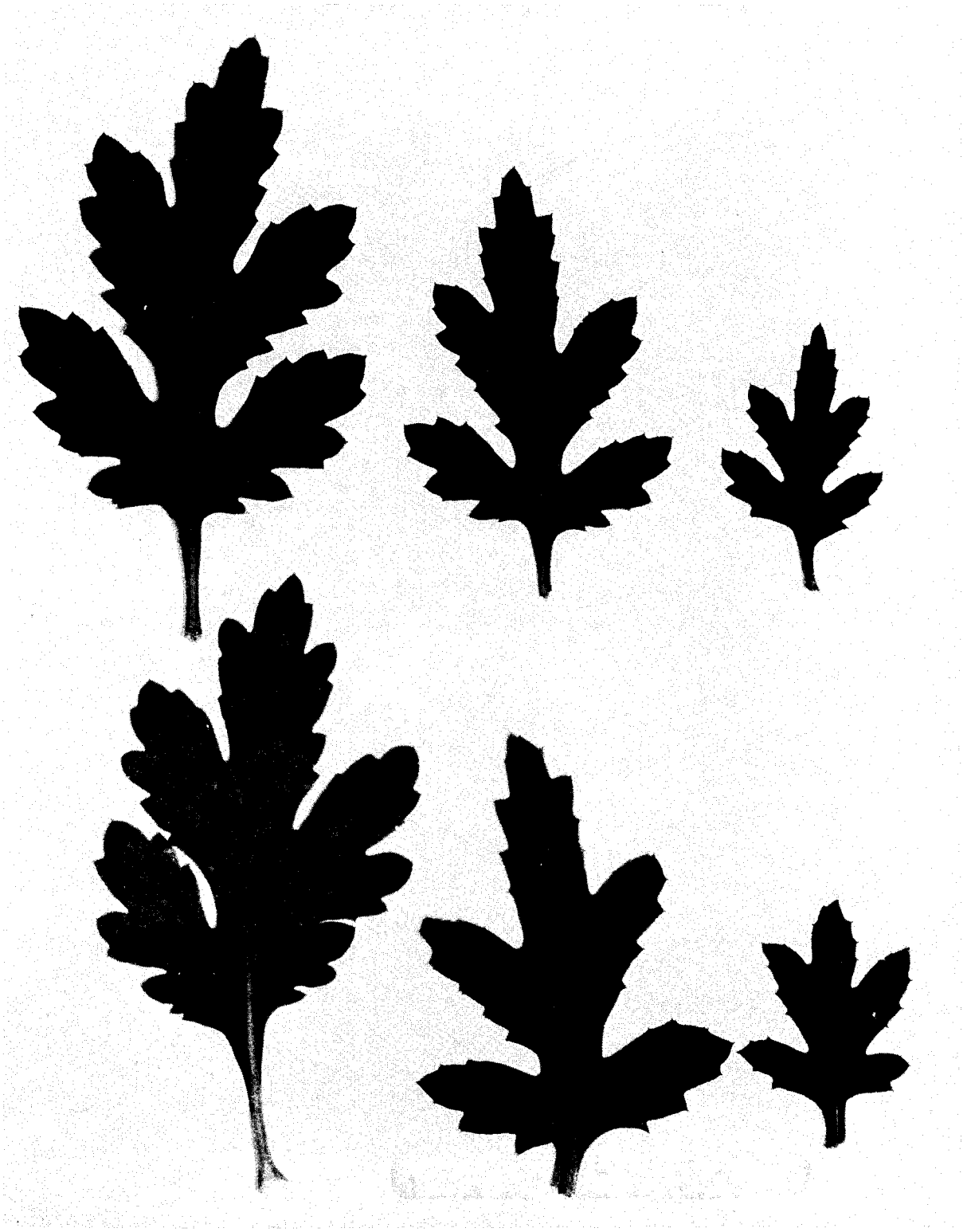

* * * * *